US010080911B2

(12) United States Patent
Zankowski et al.

(10) Patent No.: US 10,080,911 B2
(45) Date of Patent: Sep. 25, 2018

(54) KNOWLEDGE-BASED SPATIAL DOSE METRICS AND METHODS TO GENERATE BEAM ORIENTATIONS IN RADIOTHERAPY

(71) Applicant: Varian Medical Systems, Inc., Palo Alto, CA (US)

(72) Inventors: Corey Zankowski, San Jose, CA (US); Janne Nord, Espoo (FI); Maria Isabel Cordero Marcos, Espoo (FI); Joona Hartman, Espoo (FI); Jarkko Peltola, Tuusula (FI); Esa Kuusela, Espoo (FI)

(73) Assignees: Varian Medical Systems, Inc., Palo Alto, CA (US); Varian Medical Systems International AG., Cham (CH)

( * ) Notice: Subject to any disclaimer, the term of this patent is extended or adjusted under 35 U.S.C. 154(b) by 278 days.

(21) Appl. No.: 14/850,625

(22) Filed: Sep. 10, 2015

(65) Prior Publication Data

US 2017/0072220 A1    Mar. 16, 2017

(51) Int. Cl.
*A61N 5/10* (2006.01)

(52) U.S. Cl.
CPC .................................. *A61N 5/1031* (2013.01)

(58) Field of Classification Search
CPC .......................................... A61N 5/103–5/1071
See application file for complete search history.

(56) References Cited

U.S. PATENT DOCUMENTS

| | | | | |
|---|---|---|---|---|
| 2008/0004845 A1* | 1/2008 | Failla | ................... | A61N 5/1031 703/2 |
| 2009/0063110 A1* | 3/2009 | Failla | ................... | A61N 5/1031 703/2 |
| 2009/0316858 A1 | 12/2009 | Nord et al. | | |
| 2011/0029329 A1 | 2/2011 | Schweizer et al. | | |
| 2011/0122997 A1 | 5/2011 | Lu et al. | | |
| 2016/0129282 A1* | 5/2016 | Yin | ........................ | A61N 5/103 600/1 |

* cited by examiner

*Primary Examiner* — Thaddeus Cox

(57) ABSTRACT

A system for estimating a dose from a radiation therapy plan includes a memory that stores machine-readable instructions and a processor communicatively coupled to the memory, the processor operable to execute the instructions to subdivide a representation of a volume of interest into voxels. The processor also determines distances between a planned radiation field origin and each respective voxel. The processor further computes geometry-based expected (GED) metrics based on the distances, a plan parameter, and a field strength parameter. The processor sums the metrics to yield an estimated dose received by the volume of interest from the planned radiation field.

14 Claims, 13 Drawing Sheets

KNOWLEDGE-BASED SPATIAL DOSE METRICS AND METHODS TO GENERATE BEAM ORIENTATIONS IN RADIOTHERAPY

TECHNICAL FIELD

This description relates generally to the field of radiation therapy, and more particularly to radiation therapy treatment plan development.

BACKGROUND

Radiation therapy treatment plan development generally employs medical imaging, such as X-ray, computed tomography (CT), magnetic resonance imaging (MRI), or the like. Typically, a series of two-dimensional patient images, each representing a two-dimensional cross-sectional "slice" of the patient anatomy, are used to reconstruct a three-dimensional representation of a volume of interest (VOI), or structure of interest, from the patient anatomy.

The VOI typically includes one or more organs of interest, often including a planning target volume (PTV), such as a malignant growth or an organ including malignant tissue targeted for radiation therapy; a relatively healthy organ at risk (OAR) in the vicinity of a malignant growth at risk of radiation therapy exposure; or a larger portion of the patient anatomy that includes a combination of one or more PTVs along with one or more OARs. The objective of the radiation therapy treatment plan development typically aims to irradiate as much of the PTV as near the prescription dose as possible, while attempting to minimize irradiation of nearby OARs.

The resulting radiation therapy treatment plans are used during medical procedures to selectively expose precise areas of the body, such as malignant tumors, to specific doses of radiation in order to destroy the undesirable tissues. During the development of a patient-specific radiation therapy treatment plan, information generally is extracted from the three-dimensional model to determine parameters such as the shape, volume, location, and orientation of one or more PTVs along with one or more OARs.

Some existing radiation therapy planning tools have estimated irradiation doses of OARs based on the simple linear, or Euclidean, distance between the PTV and each OAR. However, additional factors typically have a significant impact on the effective radiation dose received by OARs in the general vicinity of the PTV. Existing methodologies can have drawbacks when used to develop radiation therapy plans, since existing methods and tools do not accurately account for these additional factors.

SUMMARY

According to one embodiment of the present invention, a system for estimating a dose from a radiation therapy plan includes a memory that stores machine-readable instructions and a processor communicatively coupled to the memory, the processor operable to execute the instructions to subdivide a representation of a volume of interest into a plurality of voxels. The processor also determines a plurality of distances, each of which is associated with a planned radiation field and a respective voxel. The processor further computes a plurality of metrics based on the plurality of distances, a plan parameter, and a field parameter. The processor also sums the plurality of metrics corresponding to the plurality of voxels. The summation of the plurality of metrics represents an estimated dose received by the volume of interest from the planned radiation field.

According to another embodiment of the present invention, a method for estimating a dose from a radiation therapy plan includes subdividing a representation of a volume of interest into a plurality of voxels, and determining a distance associated with a planned radiation field and a voxel. The method further includes computing a metric based on the distance, a plan parameter, and a field parameter.

According to yet another embodiment of the present invention, a method for estimating a dose from a radiation therapy plan includes generating normal vectors that emanate from points on a surface of a representation of a target volume and extend to a body surface. The method includes quantifying a dose fall-off curve along each of the normal vectors based on the radiation therapy plan. The method also includes grouping a subset of the plurality of normal vectors based on a traversed organ at risk, and determining a mean dose fall-off curve for the organ at risk based on the subset. The method further includes deriving a dose-volume histogram for the organ at risk based on the mean dose fall-off curve and a mean distance between the target volume and the organ at risk.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
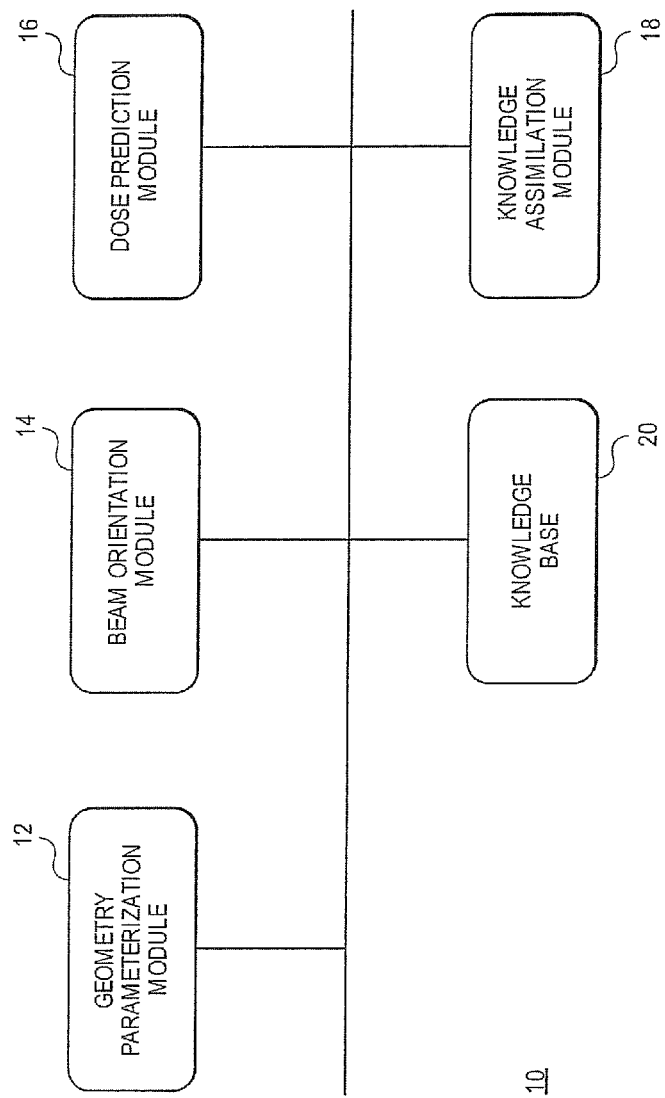
FIG. 1 is a schematic view illustrating an exemplary dose distribution planning tool that employs spatial dose metrics to generate beam orientations in order to develop and evaluate patient-specific radiation therapy treatment plans in accordance with an embodiment of the present invention.

An embodiment of the present invention is shown in FIG. 1, which illustrates an exemplary dose distribution planning tool 10 that employs spatial dose metrics to generate beam orientations in order to develop and evaluate patient-specific radiation therapy treatment plans. The dose distribution planning tool 10 includes a patient geometry parametrization module 12, a beam orientation module 14, a dose prediction module 16, a knowledge assimilation module 18 and a knowledge base 20. The dose distribution planning tool 10 correlates dose distributions achieved in actual patients in radiotherapy treatments with the underlying patient anatomy, or geometry.

The dose distribution planning tool 10 predicts the three-dimensional dose distribution for a new patient based on the patient anatomy and selects radiation beam orientations that have a relatively high probability of achieving the predicted dose distribution, which is in part a function of the beam orientation.

The patient geometry parametrization module 12 generates a set of parameters, or metrics, based on the individual patient anatomic geometry with respect to various factors that affect dose distribution. It is known in the art that the dose level outside of a target structure decreases with linear, or Euclidean, distance from the target structure. However, additional geometric features can affect dose distribution. Metrics that take into account additional geometric features offer relatively improved correlation between predicted dose distribution and structure positions in patient geometry.

Examples of expected dose metrics in addition to OAR-target proximity include but are not limited to the volume of the target structure, the volume of an organ at risk (OAR), any portion of the OAR that is not located within the field of the radiation beam, the number and orientation of applied fields, field geometry, target and OAR tissue densities, the prescription dose, and the like. For example, various metrics can take into account the number of fields that converge at each point in the patient geometry, or any organ passed through by a field before reaching the target volume. Additional metrics can account for tissue characteristics, for example, the Hounsfield unit (HU) scale can represent energy deposition and dispersion characteristics.

For example, the dose attenuation, or fall-off, profile is not symmetric, but rather, drops off much more rapidly as location extends beyond the vicinity of the target volume toward an out-of-field region. In addition, application of multiple fields with differing target dose levels at varying distances from a point in an OAR further complicate the determination of an equivalent distance using combined metrics.

An embodiment of the present invention generates metrics with respect to the target volume and OARs based on a geometrically-expectable dose (GED) distribution. GED metrics incorporate general assumptions regarding how a clinical dose delivery is organized with respect to the target shape. GED metrics also take into account the geometry of the field setup. The dose at any point in an OAR is equal to the sum of the individual contributory doses at that location due to each of the applied target-level fields.

In an embodiment, OAR geometry is included in GED metrics, for example, the number of voxels in OARs that are crossed by a field before reaching the target volume. In another embodiment, conformal dose metrics are employed, including descriptive setup and patient geometry factors. The beam orientation module 14 evaluates the patient geometry metrics and determines preferred beam geometry in the form of one or more beam orientations that meet the constraints for the target volume and OARs.

In an embodiment, the field intensity is modulated to tailor the dose distribution to the specific target form. Target anatomical features, including, for example, the shape, elongation, and position of the target with respect to multiple fields, preferred directions, or beam orientations, are defined. Thus, for example, fields that are perpendicular to the target main direction are allowed to deliver less radiation than fields that are parallel to the target main direction.

Further, in an embodiment, the intensity of radiation delivered across a field is modulated with respect to GED metrics assigned to each beamlet within a field. For example, metrics can be defined regarding the number of voxels the beamlet crosses, or the distance the beamlet travels through the patient before reaching the target volume, and the intensity of the beamlet can be adjusted according to the metrics.

The dose prediction module 16 evaluates the dose distribution with respect to a specific set of metrics and a specific grouping of beam orientations. The dose prediction module 16 employs a knowledge-based dose prediction algorithm that predicts the viable dose distribution on a structure of interest based on a set of anatomical features. The dose prediction algorithm estimates the quality of treatment plan achieved based on detailed planning for specific target geometries and field geometries.

In an embodiment, the dose prediction module 16 permits interactive definition and fine-tuning of the target volume to be treated while providing an immediate estimate of the achievable plan quality. The quality can be described, for example, by predicting the dose-volume histograms (DVHs) that would be achieved for a specific target volume. The dose prediction module 16 can facilitate decisions, for example, regarding the clinical tradeoff between the size of spatial region to be irradiated and sparing of critical organs.

In another embodiment, the dose prediction module 16 permits interactive definition and modification of the radiation field geometry while providing an immediate estimate of the achievable plan quality. Thus, independent dose optimization would not be required for each candidate target volume and field geometry. Further, in an embodiment, the dose distribution is evaluated with respect to multiple target volumes, for example, adding weighted contributions, or fractionations, corresponding to the various modified distances from an OAR to multiple target volumes with different dose levels.

In an embodiment, the geometrically expectable dose (GED) is calculated, whenever possible, using specific field geometry information, which yields a relatively accurate and meaningful definition of the dose contribution resulting from the out-of-field portion of the OAR. When the field geometry is not available a priori, equally distributed fields surrounding the patient in the isocenter plane are considered. The GED is the expected dose that a water-equivalent patient with the defined anatomical geometry would receive if the same amount of radiation were delivered to the target from each field.

In various embodiments, the GED metrics are used in dose-volume histogram (DVH) estimation, fluence estimation, or three-dimensional dose estimation. In an embodiment, estimated dose distributions based on GED metrics are compared with corresponding dose distributions actually achieved in clinical treatments to tune an actual knowledge model.

The knowledge assimilation module 18 extracts major dosimetric features from existing datasets representing the actual historical patient population. In knowledge-based dose prediction, information gleaned from actual historical plans is used to estimate the achievable dose distribution regarding a new patient. For example, patient geometry and dose information of multiple historical treatment plans is distilled into a prediction model that can be used for dose prediction without storing all of the information from the original set of plans.

The knowledge base 20 stores the existing datasets representing a historical population of actual patient anatomical and achieved dose information. The systems described herein can offer advantages such as evaluating plans with different field geometries, evaluating plans with multiple target volumes with differing dose levels, and analyzing the effect of target volume shape on dose distribution.

Figure 2:
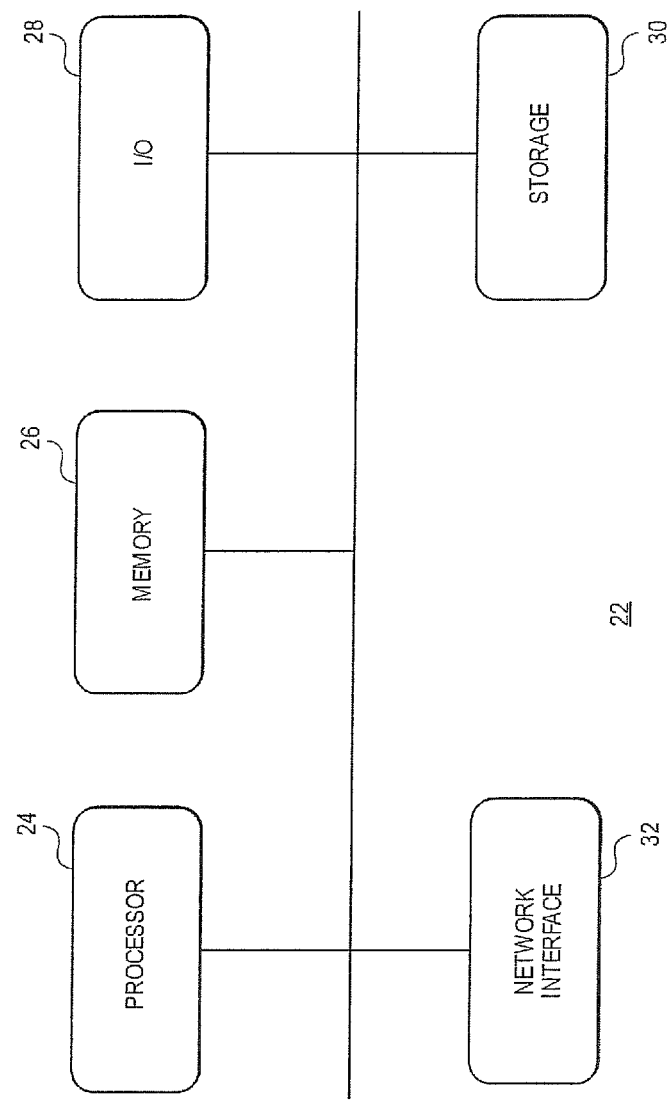
FIG. 2 is a schematic view depicting an exemplary general computing system that can implement the dose distribution planning tool of FIG. 1.

As illustrated in FIG. 2, an exemplary general computing device 22 that can be employed in the dose distribution planning tool 10 of FIG. 1 includes a processor 24, a memory 26, an input/output device (I/O) 28 storage 30 and a network interface 32. The various components of the computing device 22 are coupled by a local data link 34, which in various embodiments incorporates, for example, an address bus, a data bus, a serial bus, a parallel bus, or any combination of these.

The computing device 22 communicates information to and requests input from the user or other devices by way of the I/O 28, which in various embodiments incorporates, for example, an interactive, menu-driven, visual display-based user interface, or graphical user interface (GUI), and a pointing device with which the user may interactively input information using direct manipulation of the GUI.

The computing device 22 can be coupled to a communication network by way of the network interface 32, which in various embodiments incorporates, for example, any combination of devices—as well as any associated software or firmware—configured to couple processor-based systems, including modems, access points, network interface cards, LAN or WAN interlaces, wireless or optical interfaces and the like, along with any associated transmission protocols, as may be desired or required by the design.

The computing device 22 can be used, for example, to implement the functions of the components of the dose distribution planning tool 10 of FIG. 1. In various embodiments, the computing device 22 can include, for example, a server, a controller, a workstation, a mainframe computer, personal computer (PC), a note pad, a computing tablet, a personal digital assistant (PDA), a smart phone, a wearable device, or the like. Programming code, such as source code, object code or executable code, stored on a computer-readable medium, such as the storage 30 or a peripheral storage component coupled to the computing device 22, can be loaded into the memory 26 and executed by the processor 24 in order to perform the functions of the dose distribution planning tool 10.

Figure 3:
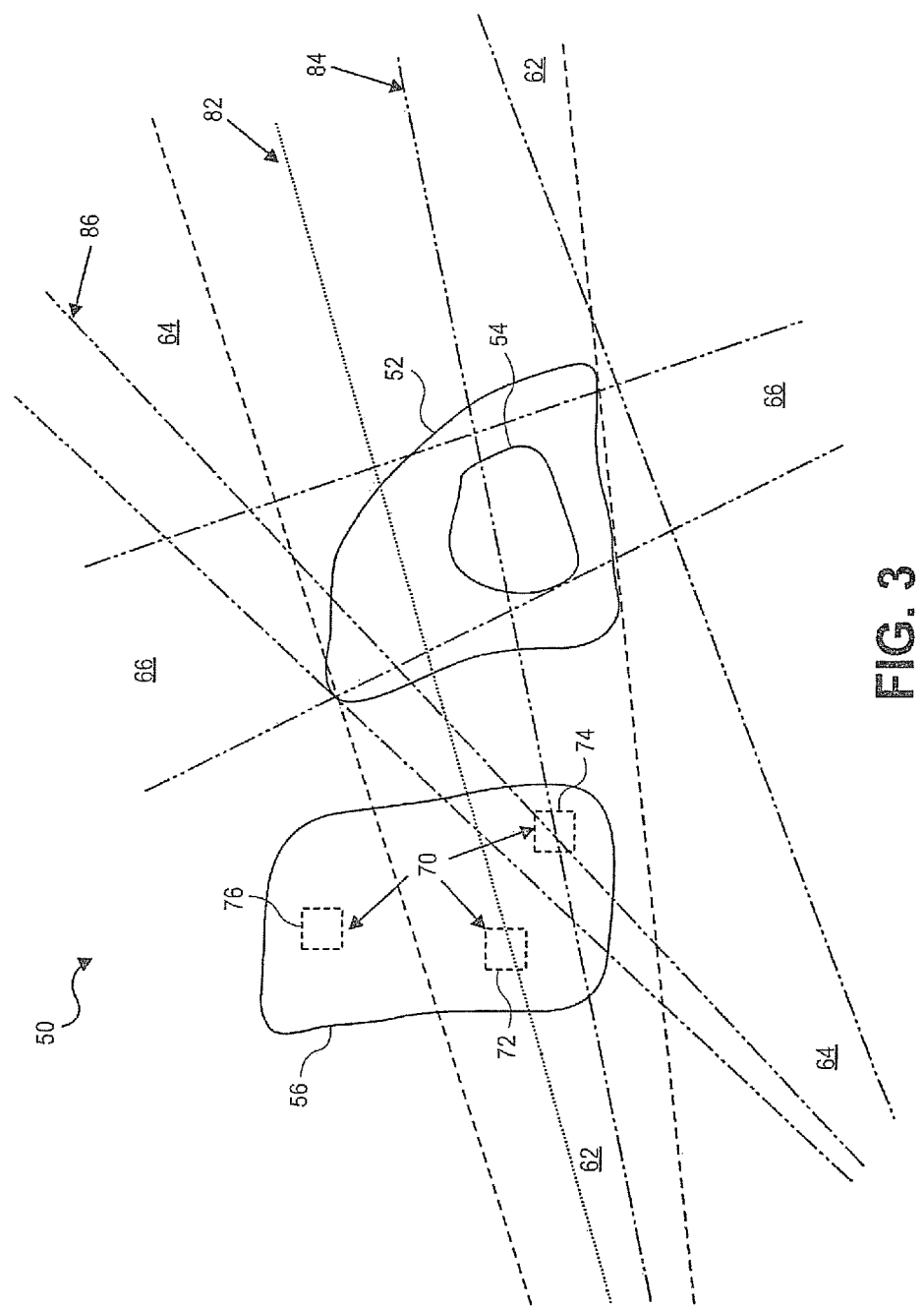
FIG. 3 is an illustration of an exemplary radiation therapy patient anatomy that can be evaluated using the dose distribution planning tool of FIG. 1.

Referring to FIG. 3, an exemplary patient anatomy 50 is depicted with several structures of interest, including a primary target volume 52, a secondary target volume 54, and an organ at risk (OAR) 56. Three planned radiation beams are also depicted, including a primary field 62, a secondary field 64 and a tertiary field 66. As used herein, the terms primary, secondary and tertiary do not refer to relative priority or magnitude, but rather, these terms are used to distinguish between the various volumes and fields.

As shown in FIG. 3, the primary field 62 and the secondary field 64 are directed toward the full scope of the primary target volume 52, and the tertiary field 66 is directed toward the scope of the secondary volume 54, which is fully enveloped by the primary target volume 52. As a result, the prescription dose planned to be delivered to the primary target volume 52, $dose_{t1}$, includes the cumulative effect of both the primary field 62 and the secondary field 64. The prescription dose planned to be delivered to the secondary target volume 52, $dose_{t2}$, includes the cumulative effect of each the primary, secondary and the tertiary fields 62, 64, 66.

The patient geometry parametrization module 12 of FIG. 1 determines a set of parameters, or metrics, to represent the OAR 56 of FIG. 3. In an embodiment, the OAR is subdivided into a number of individual volume partitions, or voxels, that are individually evaluated with regard to dose distribution. For example, three individual voxels 70 are depicted in FIG. 3. Metrics are assigned to each voxel based on the distance from each field origin to the voxel, the prescription dose of any target(s) crossed by the corresponding field fanline, and a field parameter based on the nominal energy of the planned radiation field. Thus, the metrics take into account the field position and orientation.

For example, the left voxel 72 lies within the scope of the primary field 62 along a fanline 82 that passes through the primary target volume 52. Thus, the patient geometry parametrization module 12 assigns metrics to the left voxel 72 that account for the strength of the primary field 62 and the distance from the origin (not shown) of the primary field 62 to the left voxel 72. For example, in an embodiment, a strength parameter, $\lambda_1$, that depends on the nominal energy of the primary field 62 is assigned to the left voxel 72, along with a distance parameter, $D_{11}$, that depends on the Euclidian distance from the primary field origin to the left voxel 72.

The right voxel 74 lies within the scope of both the primary field 62 and the secondary field 64. Another fanline 84 of the primary field 62 passing through the right voxel 74 passes through both the primary target volume 52 and the secondary target volume 54. A fanline 86 of the secondary field 64 passing through the right voxel 74 also passes through the primary target volume 52. Thus, the patient geometry parametrization module 12 assigns metrics to the right voxel 74 that account for the strength of the primary field 62, the strength of the secondary field 64, the distance from the primary field origin to the right voxel 74, the distance from the secondary field origin (not shown) to the right voxel 74, and the prescription doses.

For example, in an embodiment, the strength parameter, $\lambda_1$, that depends on the nominal energy of the primary field 62, as well as another strength parameter, $\lambda_2$, that depends on the nominal energy of the secondary field are assigned to the right voxel 74. In addition, a distance parameter, $D_{12}$, that depends on the Euclidian distance from the primary field origin to the right voxel 74, as well as another distance parameter, $D_{22}$, that depends on the Euclidian distance from the primary field origin to the right voxel 74 are assigned to the right voxel 74.

The dose prediction module 16 of FIG. 1 evaluates the planned dose distribution delivered to the OAR by evaluating the expected dose contribution received at each defined voxel in the OAR. In an embodiment, the geometrically-expected dose received at the left voxel 72 of FIG. 3 is calculated using the metrics assigned to the left voxel 72, for example, the strength parameter, $\lambda_1$, and the distance parameter, $D_{11}$, in the following formula:

$$GED_1 = dose_{t1}\left(\frac{(D_{11})e^{(-\lambda_1 D_{11})}}{(D_{11})^2}\right) \quad (1)$$

Further, the geometrically-expected dose received at the right voxel 74 is calculated using the metrics assigned to the right voxel 74, for example, the strength parameters, $\lambda_1$ and $\lambda_2$, and the distance parameters, $D_{12}$ and $D_{22}$. The geometrically-expected dose contribution at the right voxel 74 due to the primary field 62 is calculated using the following formula:

$$GED_{12} = dose_{t1}\left(\frac{(D_{12})e^{(-\lambda_1 D_{12})}}{(D_{12})^2}\right) + \quad (2a)$$

$$(dose_{t2} - dose_{t1})\left(\frac{(D_{12})e^{(-\lambda_1 D_{12})}}{(D_{12})^2}\right)$$

$$= dose_{t2}\left(\frac{(D_{12})e^{(-\lambda_1 D_{12})}}{(D_{12})^2}\right) \quad (2b)$$

The geometrically-expected dose contribution at the right voxel 74 due to the secondary field 64 is calculated using the following formula:

$$GED_{22} = dose_{t1}\left(\frac{(D_{22})e^{(-\lambda_2 D_{22})}}{(D_{22})^2}\right) \quad (3)$$

As a result, the total geometrically-expected dose received at the right voxel 74 due to both the primary and secondary fields 62, 64 is provided by calculating the sum of the contributions of both fields 62, 64, for example, summing the results of formulas (2) and (3) above in the following formula:

$$GED_2 = dose_{t2}\left(\frac{(D_{12})e^{(-\lambda_1 D_{12})}}{(D_{12})^2}\right) + dose_{t1}\left(\frac{(D_{22})e^{(-\lambda_2 D_{22})}}{(D_{22})^2}\right) \quad (4)$$

On the other hand, the out-of-field voxel 76 lies outside all three fields 62, 64, 66. Since no field fanlines cross the out-of-field voxel 76, none of the three fields 62, 64, 66 has any contribution to the dose distribution at the out-of-field voxel 76. Thus, the geometrically-expected dose received at the out-of-field voxel 76 is zero (0). The dose prediction module 16 derives the achievable dose-volume histogram (DVH) regarding the OAR 36 from the summation of the contributions at all of the voxels of the OAR 36 from all of the planned radiation fields.

Figure 6:
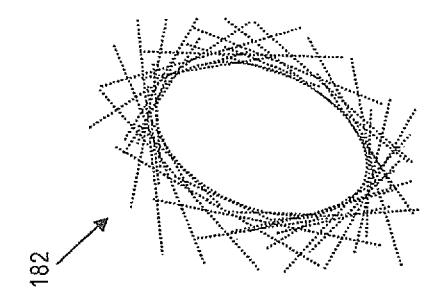
FIG. 6 is an illustration of an exemplary set of tangential lines from a curve.
Figure 5:
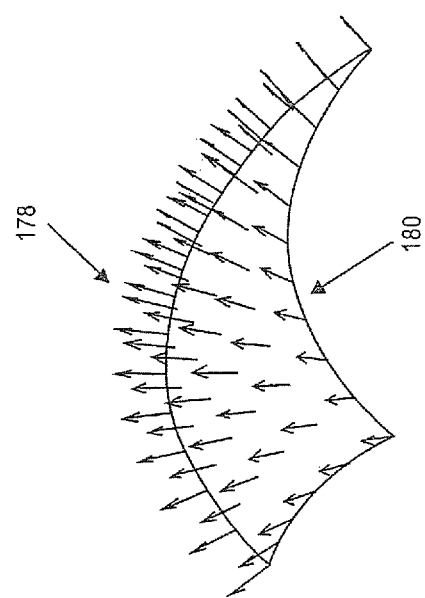
FIG. 5 is an illustration of an exemplary set of normal vectors on a complex surface.
Figure 4:
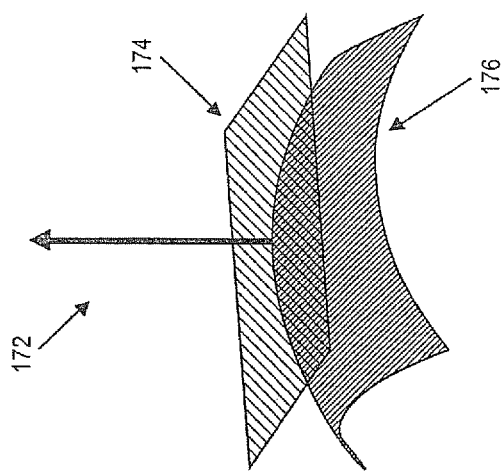
FIG. 4 is an illustration of an exemplary normal vector and tangential plane of a curved surface.

FIG. 4 shows a normal vector, $\hat{n}_{PTV}$ 172, and a tangent plane, $T_1$ 174, on the surface of a planning target volume 176. FIG. 5 illustrates a set of normal vectors 178 from a complex planning target volume surface 180. FIG. 6 illustrates tangential lines 182 from a two-dimensional curve.

Figure 7:
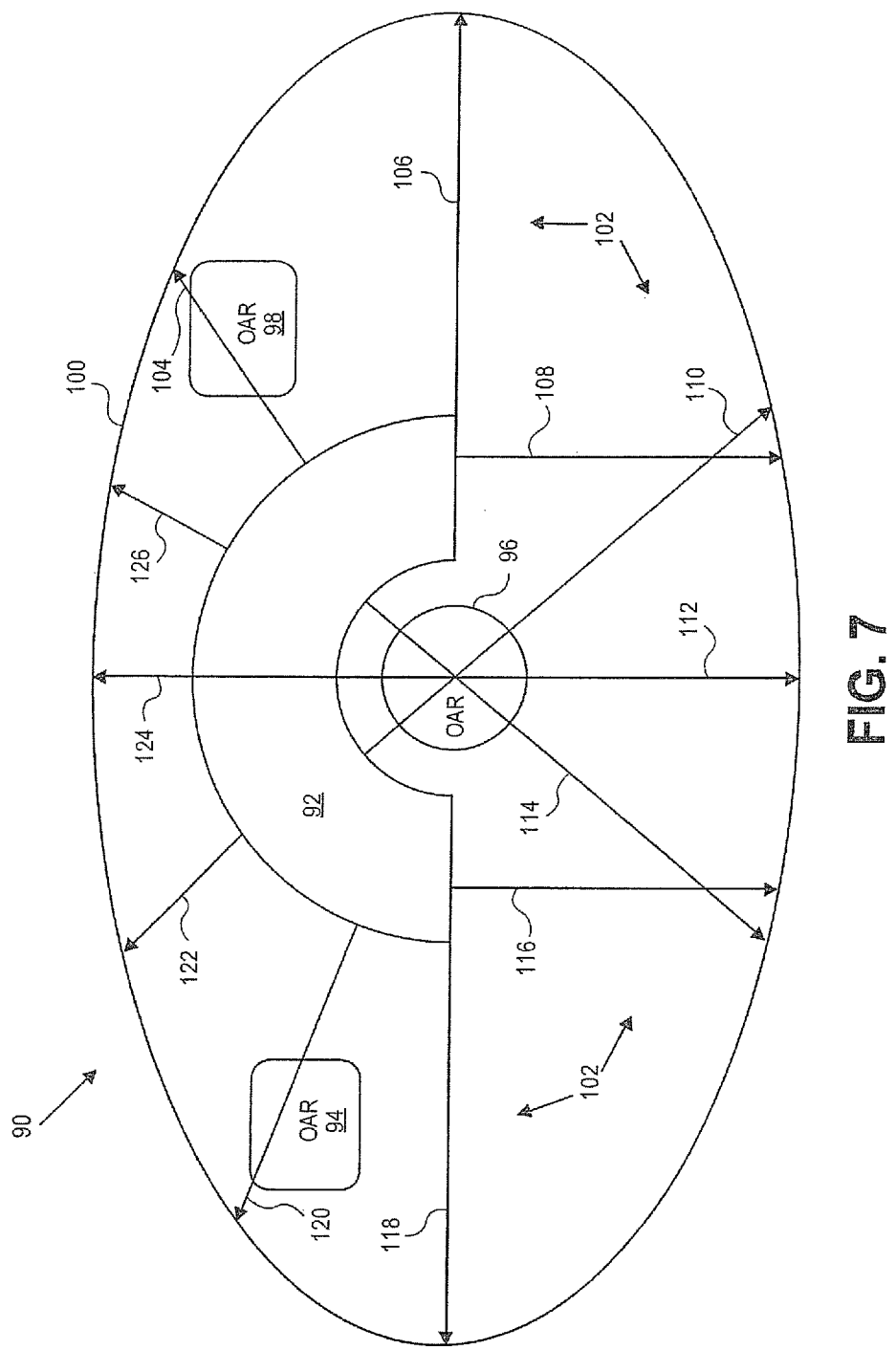
FIG. 7 is an illustration of another exemplary radiation therapy patient anatomy that can be evaluated using the dose distribution planning tool of FIG. 1.

Referring now to FIG. 7, another exemplary patient anatomy 90 is depicted with several structures of interest, including a target volume 92, a primary organ at risk (OAR) 94, a secondary OAR 96, and a tertiary OAR 98. An embodiment of the present invention correlates achieved dose distributions in actual historical patient radio therapy treatment plans to specific underlying patient anatomy and stores the resultant correlation information in the knowledge base 20 of FIG. 1. The correlation information in the knowledge base 20 is accessed in order to predict three-dimensional dose distribution for new patients based on patient anatomy.

Normal vectors are computed originating at multiple points on the surface of the target volume 92 to the body surface 100 of the patient. For example, in an embodiment, the patient geometry parametrization module 12 of FIG. 1 computes normal vectors on a grid along the three-dimensional surface of the target volume 92. As a simplified example, normal vectors 102, or rays, are computed at various points along the surface of a cross-section of the target volume 92. Each normal vector 102 is traced from the surface of the target volume 92 in a direction that is orthogonal to the localized area of the surface of the target volume 92 immediately surrounding the point from which the normal vector 102 originates.

The dose prediction module 16 computes the dose along the normal vectors 102 with respect to the distance from the surface of the target volume 92. For example, in an embodiment, the dose is computed along the normal vectors 102 from within the target volume 92 to the body surface 100. Thus, the entire dose fall-off curve is determined along each normal vector 102 until exiting the body contour. For example, the historical patient population-derived average dose falloff curve is quantified along the ray emanating along the normal vector 102.

Figure 8:
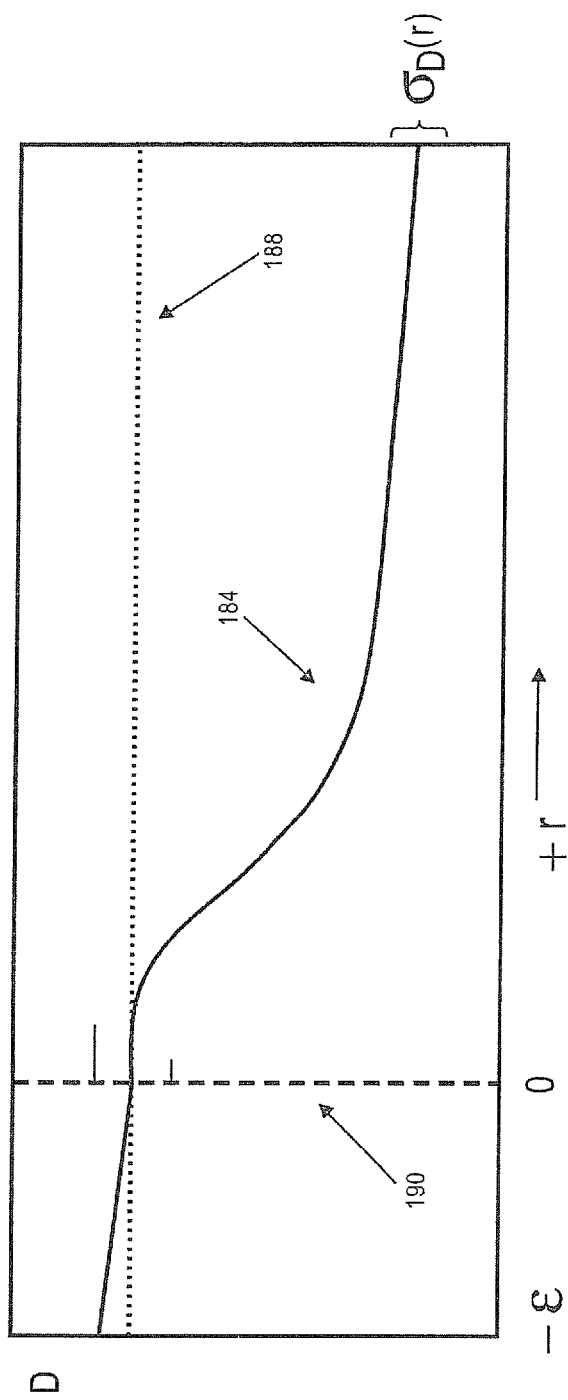
FIG. 8 is an exemplary dose curve from within a planning target volume to the body surface.

The normal vectors 102 are grouped according to the organ(s) at risk intersected by each normal vector 102. As illustrated in FIG. 8, the mean dose, D(r) 184, along the portion of each of the normal vectors 102 intersecting an OAR is recorded. For example, the mean dose is calculated for the portion of normal vector 104 passing through the OAR 98; the mean dose is calculated for the portion of the normal vector 122 passing through the OAR 94; and the mean doses are calculated for the portions of the normal vectors 110, 112, 114 passing through the OAR 96. The prescription dose 188 and the PTV surface 190 are indicated in FIG. 8.

In addition, the population variations, $\sigma_D(r)$, in D(r) are tracked for each OAR 94, 96, 98. In an embodiment, the dose prediction module 16 uses the mean doses for each OAR 94, 96, 98 to produce a rapid estimation of achievable three-dimensional dose for the respective OAR 94, 96, 98.

Rays are traced along the normals of the target surface, and the three-dimensional dose distribution is estimated. The dose along the normal ray between PTV and OAR is a principle component characterizing the three-dimensional dose distribution of a radiotherapy plan. Collapsing the three-dimensional data into quasi-directional two-dimensional plots is as efficient, but more descriptive, than collapsing into dose-volume histogram plats. Modeling is simple, and has proven to be effective. Statistically-modeled results can be used to refine the results and performance of the model.

The dose prediction module 16 derives the achievable dose-volume histogram (DVH) regarding the OARs 94, 96, 98 from the dose fall-off curves associated with the respective normal vectors 104, 110, 112, 114, 122 and the distances between the OARs 94, 96, 98 and the target volume 92. The dose prediction module 16 computes the derivatives of the dose fall-off curves for each normal vector 102, as well as the dose gradient for the mean dose, $$\vec{g} = \frac{\Delta D}{\Delta r},$$

corresponding to each OAR 94, 96, 98, and identifies areas requiring strong dose gradients. In an alternative embodiment, the three-dimensional data is collapsed into quasi-directional two-dimensional plots, which retain more descriptive information than DVH plots.

Figure 9:
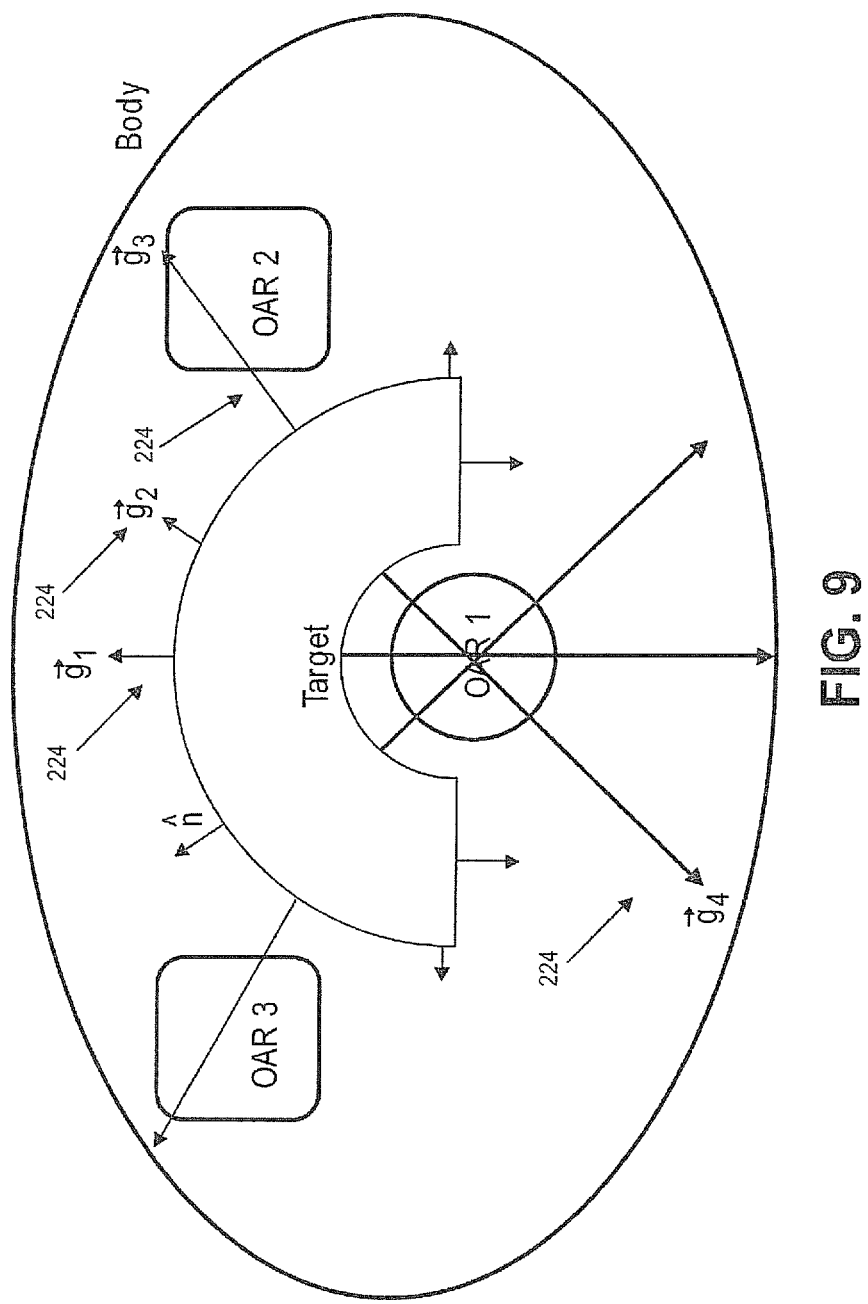
FIG. 9 is an illustration of exemplary dose gradient vectors from a planning target volume in a radiation therapy patient anatomy.

Referring to FIG. 9, the radial dose gradients 224 are estimated along each ray. The dose gradient, $$\vec{g} = \frac{\Delta D}{\Delta r},$$

is computed in each normal direction, where D=dose and r=radial distance. Vectors are bigger in directions that have stronger gradients. The derivative of the dose fall-off curves $$\frac{\Delta D}{\Delta r}$$

can be computed.

$$\frac{\Delta D}{\Delta r}$$

identifies zones where high gradients are needed to achieve the desired or expected radiotherapy plan.

Figure 10:
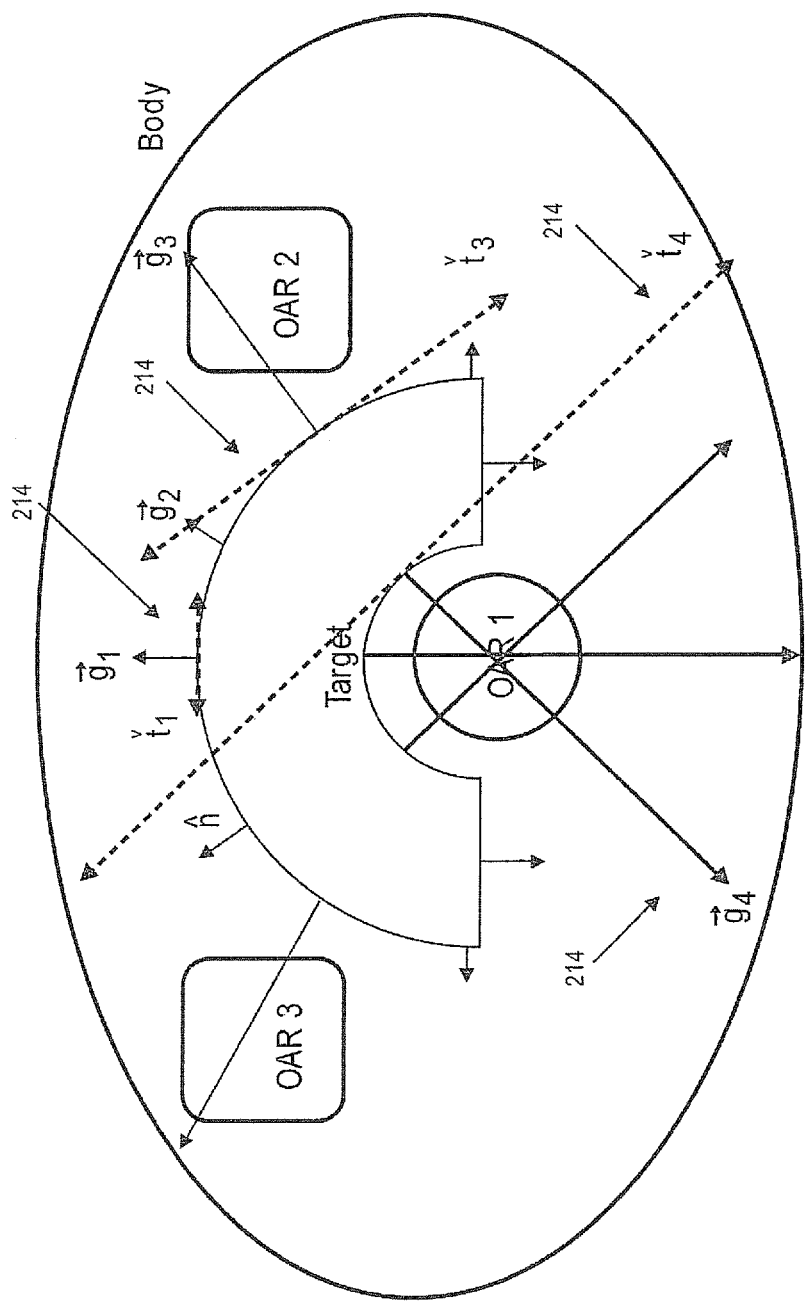
FIG. 10 is an illustration of exemplary perpendiculars to dose gradient vectors.

Referring to FIG. 10, perpendiculars 214 to each gradient vector identify beam orientations, where $\vec{t} = \|\vec{g}\| =$ the arc plane perpendicular to $\vec{g}$. The derivative of the dose fall-off curves $$\frac{\Delta D}{\Delta r}$$

are computed.

$$\frac{\Delta D}{\Delta r}$$

identities zones where high gradients are needed to achieve the desired or expected radiotherapy plan.

The beam orientation module 14 back-projects the dose gradient strength perpendicular to the planning target volume normal direction to identify preferred beam orientations. The beam orientation module 14 determines perpendicular vectors with respect to each gradient vector tangent to the surface of the target volume. Beam orientations that are perpendicular to strong gradient directions can be emphasized to reinforce the gradient. Normals with gradient indicate arc planes of preference for beam orientation. Gradient strength can be projected along perpendiculars onto a 4 pi sphere into a heat map that predicts beam orientation or trajectory.

Figures 11, 12, 13:
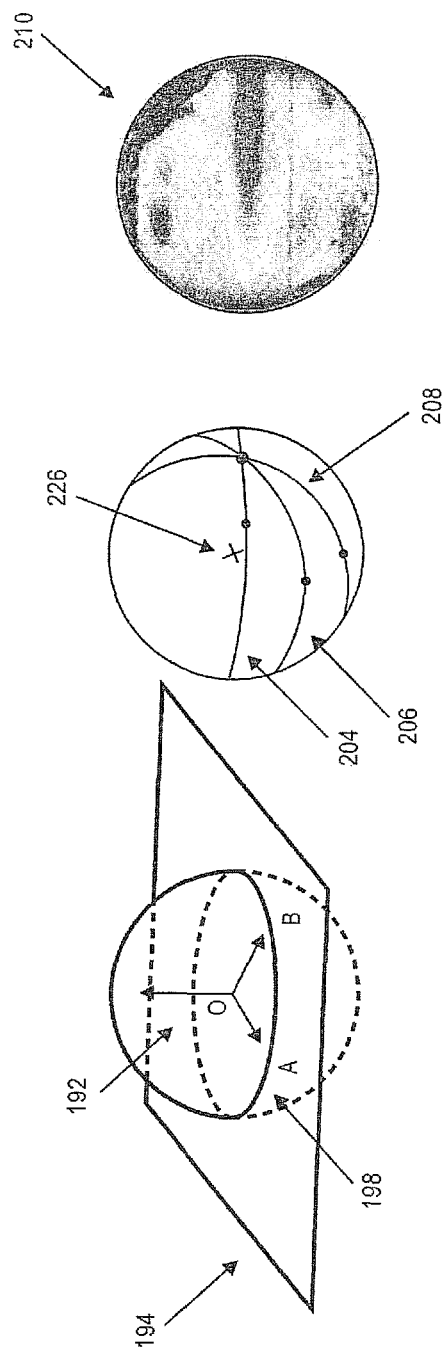
FIG. 11 is an illustration of an exemplary projection of a dose gradient onto a sphere.
FIG. 12 is an illustration of exemplary meridians projected onto a sphere from dose gradients.
FIG. 13 is an illustration of an exemplary thermal map representing projected dose gradients.

For example, as shown in FIG. 11, the beam orientation module 14 projects the dose gradient 192, $$\vec{g} = \frac{\Delta D}{\Delta r},$$

of the mean dose, D(r), for each normal vector 102, n̂, onto the plane 194 perpendicular to the normal vector crossing the target volume isocenter. The plane 194 (A×B) has a normal along the gradient direction. The plane 194 forms a meridian 198 on a sphere 200 about the isocenter 202 of the target volume.

FIG. 12 shows gradients projected to meridians 204, 206, 208 around a sphere isocenter 226. The beam orientation module 14 interpolates between the meridians resulting from all of the normal vectors 102, and creates a preference matrix, for example, the thermal plot or map 210 illustrated in FIG. 13. The resulting preference matrix indicates preferred beam orientations to achieve high dose gradients.

Figure 14:
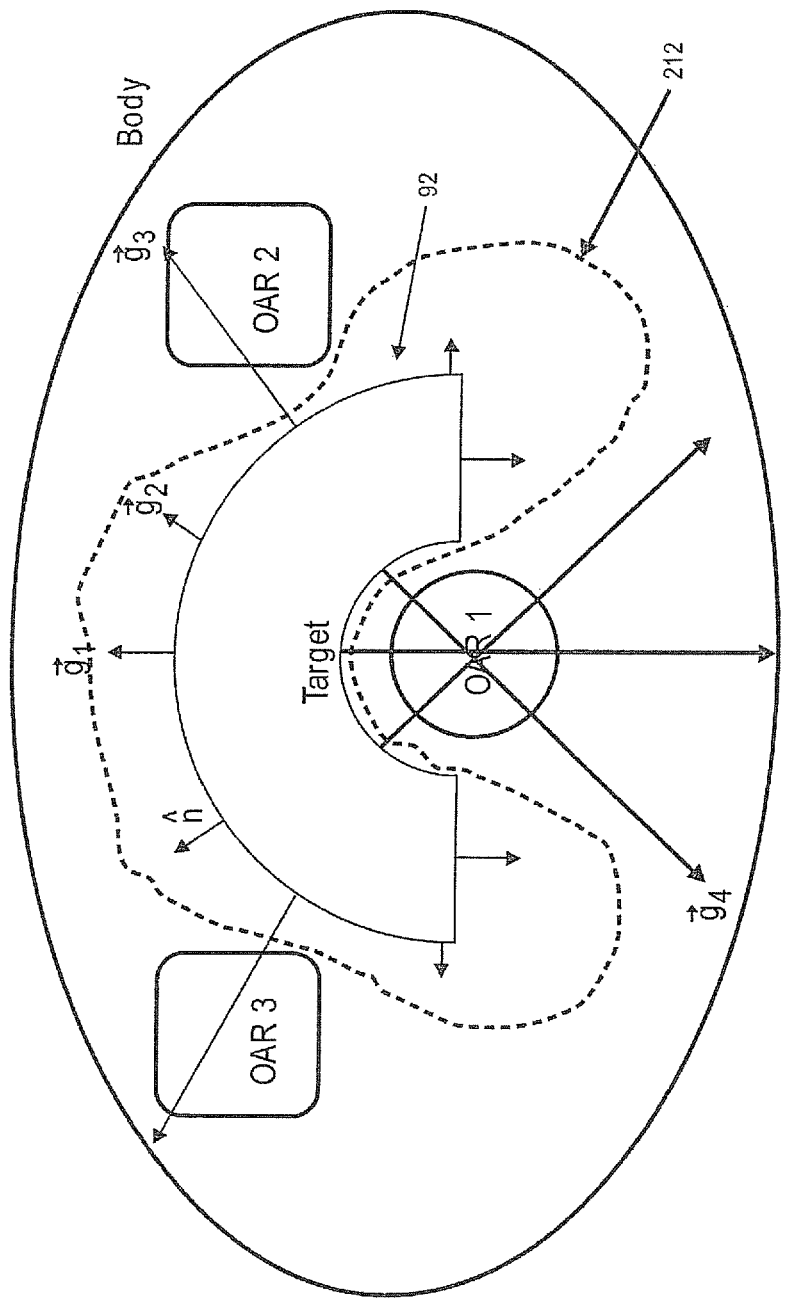
FIG. 14 is an illustration of an exemplary custom bounding box.

Referring to FIG. 14, a custom motion management bounding box 212 is constructed around the target volume 92. In each normal direction, the bounding margin (Δr) for an acceptable dose error (Δd) is computed as follows:

$$\Delta r = \frac{\Delta d}{\frac{\Delta D}{\Delta r}}$$

The beam orientation module 14 computes custom bounding shapes, or isoconfidence boundaries, around the target volume 92 reflecting the dose sensitivity to target position error. The dose gradient along the respective normal vector is used as the basis for dose-sensitivity analysis as a function of distance to the target volume 92. The custom bounding box can be constructed based on the distance margin at each normal vector location as indicated by the ratio of the maximum acceptable dose uncertainty to the gradient along the respective normal vector. The beam orientation module 14 identifies beam orientations that are most sensitive to target motion in order to drive motion management strategy as a function of beam orientation.

Figure 15:
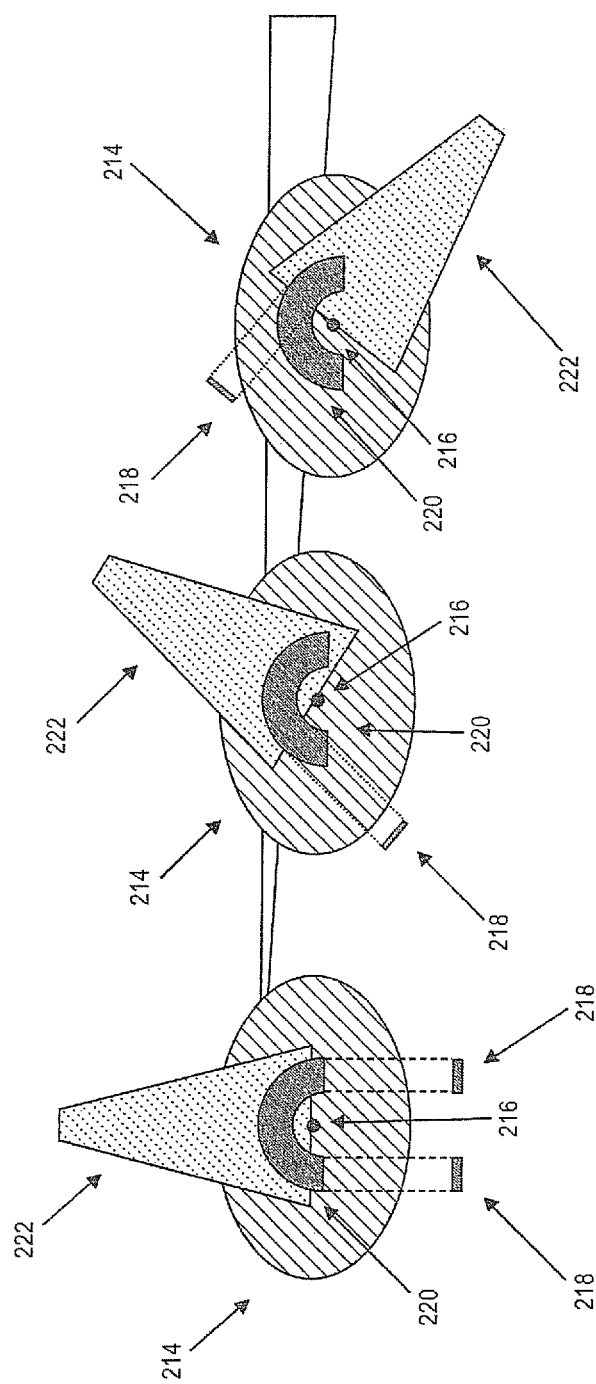
FIG. 15 is an illustration of exemplary planes through isocenters.

Referring to FIG. 15, three illustrations show planes 214 passing through isocenters 216 of planning target volumes. From each beam orientation, a two-dimensional projection 218 of the target 220 intersected by a plane 214 perpendicular to the beam 222 is computed.

The knowledge assimilation module 18 records achieved dose profiles associated with actual historical patient treatment plans, and tracks population variations in dose with respect to the distance from the surface of the target volume 92. OARs intercepted by each surface normal ray trace are determined, and a curve describing relative dose as a function of distance from PTV surface along the normal direction is stored into a D(r) plot for each OAR intercepted by the ray. For retrieval, the median achieved dose from the stored D(r) histogram to each pixel along the ray is assigned according to its distance from the PTV.

For example, normal vectors 106, 108, 116, 118, 122, 124, 126 do not traverse any OARs, so the resulting dose profiles are stored in the body dose-distance plot in the knowledge base 20. Since normal vector 120 traverses OAR 94, the resultant dose profile is stored in the OAR 94 dose-distance plot and in the body dose-distance plot in the knowledge base 20. Similarly, normal vector 104 traverses OAR 98, so the resultant dose profile is stored in the OAR 98 dose-distance plot and in the body dose-distance plot in the knowledge base 20. Normal vectors 110, 112, 114 traverse the OAR 96, so the resultant dose profiles are stored in the OAR 96 dose-distance plot and in the body dose-distance plot in the knowledge base 20.

In an alternative embodiment, a Boolean step can be used to create a body-only category for additional refinement. In another alternative embodiment, the surface of the target volume 92 is regularized using a normal vector smoothing methodology. In yet another alternative embodiment, the ray is traced from the surface of the PTV to the body contour in the direction of the normal, and traced in the negative direction from the PTV surface to the medial surface of the PTV.

Figure 16:
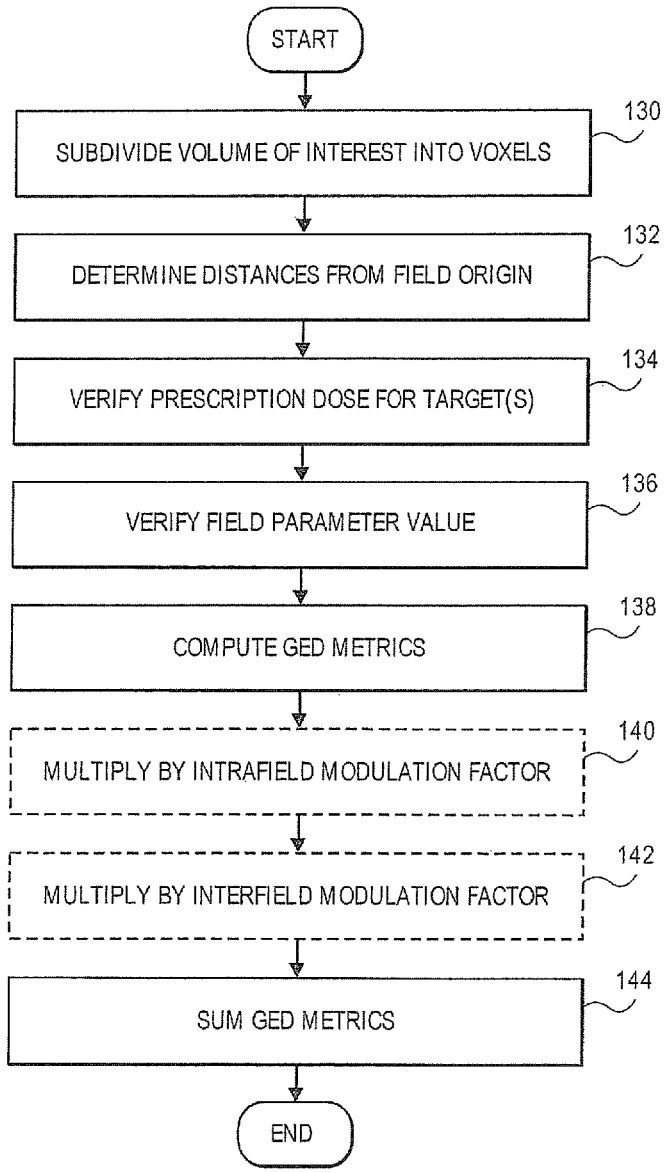
FIG. 16 is flowchart depicting an exemplary process flow for employing spatial dose metrics to develop and evaluate patient-specific radiation therapy treatment plans in accordance with an embodiment of the present invention.

Referring now to FIG. 16, an exemplary process flow is illustrated that may be performed, for example, by the dose distribution planning tool 10 of FIG. 1 to implement an embodiment of the method described in this disclosure for employing spatial dose metrics to generate beam orientations in order to develop and evaluate patient-specific radiation therapy treatment plans. The process begins at block 130, where a volume of interest, such as an organ at risk (OAR), is subdivided into a group of voxels, for example, equal-sized, three-dimensional units, as described above.

As further described above, in block 132, the distance from the planned radiation beam field origin to each voxel is determined. The prescription dose for each target is ascertained, in block 134, and the value of a parameter that depends on the nominal energy of each field is ascertained, in block 136.

In block 138, as explained above, geometry-based expected dose (GED) metrics are computed for all voxels with respect to each planned radiation field and each target traversed by a fanline passing through the respective voxels. The GED metrics may be optionally multiplied by an intrafield modulation factor, in block 140. The GED metrics may be optionally multiplied by an interfield modulation factor, in block 142. Components shown with dashed lines in FIG. 16 are optional items that may not be included in all implementations.

In block 144, the GED metrics are summed for all voxels in the volume of interest with respect to each field. The summation of the GED metrics provides an estimation of the total dose received by the volume of interest in the planned radiation therapy.

Figure 17:
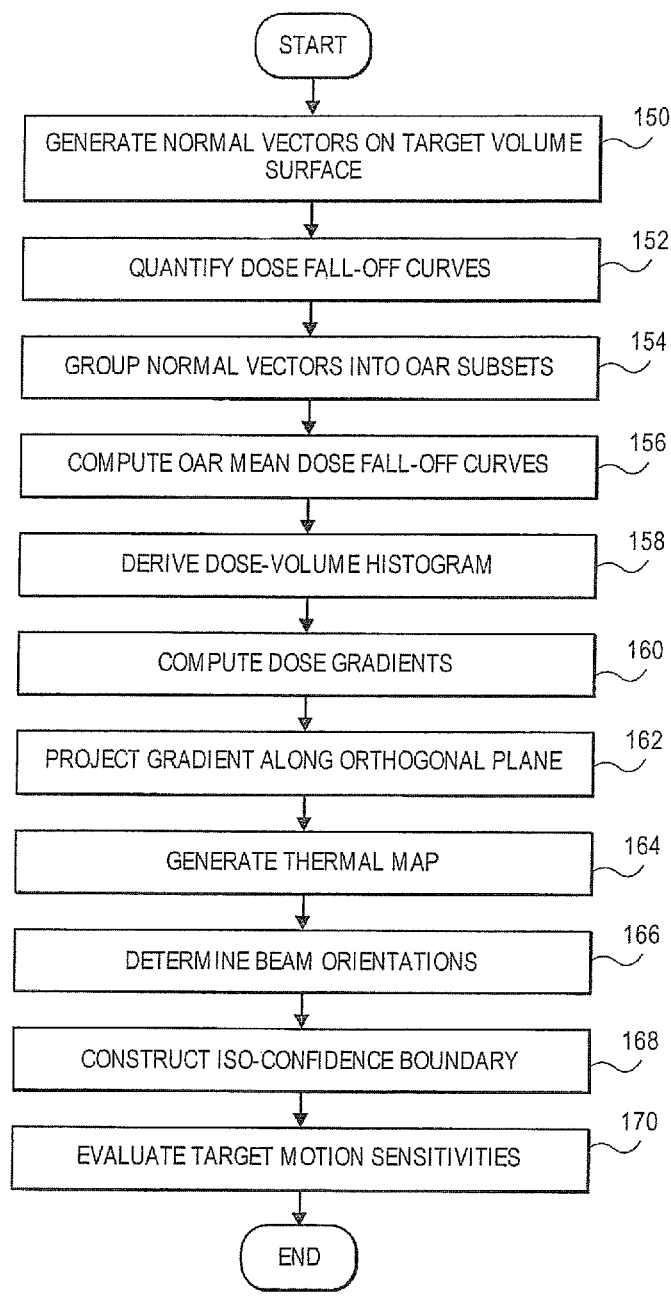
FIG. 17 is a flowchart depicting another exemplary process flow for employing spatial dose metrics to develop and evaluate patient-specific radiation therapy treatment plans in accordance with an embodiment of the present invention.

Referring now to FIG. 17, another exemplary process flow is illustrated that may be performed, for example, by the dose distribution planning tool 10 of FIG. 1 to implement an embodiment of the method described in this disclosure for employing spatial dose metrics to generate beam orientations in order to develop and evaluate patient-specific radiation therapy treatment plans. The process begins at block 150, where normal vectors are generated emanating from multiple points, for example, forming a grid, on the surface of a target volume, as described above. The normal vectors extend, for example, from the target volume surface to the body surface of the patient.

As further described above, in block 152, a dose fall-off curve is quantified along each of the normal vectors until exiting the body based on the radiation therapy plan historical results of actual patient therapy plans. The normal vectors are grouped into subsets that traverse each organ at risk (OAR), in block 154. Based on the subset of normal vectors that pass through each OAR, as explained above, mean dose is computed for each OAR and for the population, in block 156, which can be used to provide a rapid estimation of the achievable three-dimensional dose. In block 158, an achievable dose-volume histogram is derived for the OARs based on the mean dose for each OAR and the mean distance between the target volume and each OAR, as further explained above.

In block 160, the dose gradient for the mean dose for each OAR is computed based on the dose falloff curve along each of the normal vectors, and areas needing strong gradients are identified. The dose gradients are projected along a plane that is orthogonal to each normal vector, in block 162. For example, in an embodiment, the dose gradients are projected along tangential planes at the surface of the target volume.

In block 164 a preference matrix, such as a thermal map or plot, is generated based on the intersections of the projected dose gradients at the surface of a sphere. Reasonable beam trajectories are derived from the thermal surface map. In block 166, preferred beam orientations are determined based on relatively high dose gradient areas of the preference matrix.

Further, in block 168, an isoconfidence boundary is constructed around the target volume based on the dose gradients to estimate confidence margins. Custom bounding shapes are computed around the planning target volume without full dose calculation. Dose sensitivity to target position error. In block 170, the sensitivity of beam orientations with respect to target volume motion or uncertain anatomy is evaluated based on the isoconfidence boundary. The results drive motion management strategy as a function of beam orientation.

Aspects of this disclosure are described herein with reference to flowchart illustrations or block diagrams, in which each block or any combination of blocks can be implemented by computer program instructions. The instructions may be provided to a processor of a general purpose computer, special purpose computer, or other programmable data processing system to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that including one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, may be embodied in hardware, in software (including firmware, resident software, micro-code, etc.), or in any combination of software and hardware, including computer program products embodied in a computer-readable medium having computer-readable program code embodied thereon.

In this respect, any combination of one or more computer readable media may be utilized, including, but not limited to, an electronic, magnetic, optical, electromagnetic, infrared, or semiconductor system, apparatus, or device, or any suitable combination of these. In the context of this disclosure, a computer readable storage medium may include any tangible medium that is capable of containing or storing program instructions for use by or in connection with a data processing system, apparatus, or device.

Computer program code for carrying out operations regarding aspects of this disclosure may be written in any combination of one or more programming languages. The program code may execute entirely on an individual personal computer, as a stand-alone software package, partly on a client computer and partly on a remote server computer, entirely on a remote server or computer, or on a cluster of distributed computer nodes.

It will be understood that various modifications may be made. For example, useful results still could be achieved if steps of the disclosed techniques were performed in a different order, and/or if components in the disclosed systems were combined in a different manner and/or replaced or supplemented by other components. Accordingly, other implementations are within the scope of the following claims.

What is claimed is:

1. A method executed on a computing device, the method for estimating a dose and developing a radiation therapy plan, the method comprising:
   executing, with a processor of the computing device, a dose distribution planning tool stored as programming code in a computer-readable medium of the computing device, wherein said executing comprises:
   subdividing a representation of a volume of interest into a first plurality of voxels;
   determining a first distance between an origin of a first planned radiation field of a radiation beam and a first voxel of the first plurality of voxels that is traversed by the first planned radiation field;
   computing a first metric based on the first distance, a prescription dose associated with a target volume outside the volume of interest, and a first field parameter; and
   evaluating the first metric and determining a beam orientation for delivering the prescription dose to the target volume, wherein said determining a beam orientation comprises including the first planned radiation field in the radiation therapy plan if the first metric satisfies a dose constraint for the volume of interest.

2. The method of claim 1, wherein a fanline of the first planned radiation field traverses the first voxel and the target volume.

3. The method of claim 1, wherein the first field parameter comprises a strength parameter corresponding to a nominal energy level of the first planned radiation field.

4. The method of claim 1, wherein the volume of interest corresponds to an organ at risk with respect to the radiation therapy plan.

5. The method of claim 1, wherein the first metric represents a discrete contribution at the first voxel to an estimated dose received by the volume of interest.

6. The method of claim 1, further comprising:
   determining a plurality of distances, each of which is associated with the first planned radiation field and a respective voxel of the first plurality of voxels, the plurality of distances including the first distance;
   computing a plurality of metrics based on the plurality of distances, one or more plan parameters associated with one or more target volumes traversed by the first planned radiation field, and the first field parameter, the one or more plan parameters including the first plan parameter; and
   summing the plurality of metrics corresponding to the first plurality of voxels, the plurality of metrics including the first metric.

7. The method of claim 6, wherein the summation of the plurality of metrics represents an estimated dose received by the volume of interest from the first planned radiation field.

8. The method of claim 1, further comprising:
   computing a second metric based on the first distance, a second plan parameter associated with a second target volume traversed by a fanline of the first planned radiation field that traverses the first voxel, and the first field parameter, wherein the second plan parameter comprises a second prescription dose associated with the second target volume; and
   summing the first metric and the second metric, wherein the resulting summation represents an estimated dose received by the first voxel from the first planned radiation field.

9. The method of claim 1, further comprising:
   determining a second distance between an origin of a second planned radiation field of a radiation beam and the first voxel; and
   computing a second metric based on the second distance, the prescription dose, and a second field parameter, wherein the first field parameter comprises a strength parameter corresponding to a nominal energy level of the first planned radiation field, and wherein the second field parameter comprises a strength parameter corresponding to a nominal energy level of the second planned radiation field.

10. The method of claim 1, further comprising:
    subdividing a representation of a second volume of interest into a second plurality of voxels;
    determining a plurality of distances, each of which is associated with the first planned radiation field and a respective voxel of the second plurality of voxels;
    computing a plurality of metrics based on the plurality of distances, one or more plan parameters associated with one or more target volumes traversed by the first planned radiation field, and the first field parameter; and
    summing the plurality of metrics corresponding to the second plurality of voxels.

11. The method of claim 1, wherein said evaluating comprises:
    generating a plurality of normal vectors that emanate from a plurality of points on a surface of a representation of the target volume and extend to a body surface;
    quantifying a dose fall-off curve along each of the normal vectors based on the radiation therapy plan;
    grouping a subset of the plurality of normal vectors based on the volume of interest;
    determining a mean dose fall-off curve for the volume of interest based on the subset; and
    deriving a dose-volume histogram for the volume of interest based on the mean dose fall-off curve and a mean distance between the target volume and the volume of interest.

12. The method of claim 11, wherein said quantifying the dose fall-off curve along each of the normal vectors comprises accessing stored patient results associated with historical therapy plans.

13. The method of claim 11, further comprising:

for each normal vector of the normal vectors, computing a dose gradient based on the dose fall-off curve along said each normal vector;

for said each normal vector of the normal vectors, projecting the dose gradient for said each normal vector along a plane that is orthogonal to said each normal vector to produce projected dose gradients;

generating a preference matrix on the surface of a sphere based on the projected dose gradients; and determining preferred beam orientations based on the preference matrix.

14. The method of claim 11, further comprising:

computing a dose gradient corresponding to each of the normal vectors based on the dose fall-off curve along each of the normal vectors;

constructing a boundary around the target volume based on dose gradients resulting from said computing; and evaluating a sensitivity of the beam orientation with respect to a target volume motion based on the boundary.

\* \* \* \* \*